United States Patent
McAleer et al.

[11] 4,115,010
[45] Sep. 19, 1978

[54] AUTOMATED PLATE READER

[75] Inventors: William J. McAleer, Ambler; William M. Hurni, North Wales, both of Pa.

[73] Assignee: Merck & Co., Inc., Rahway, N.J.

[21] Appl. No.: 655,318

[22] Filed: Feb. 3, 1976

[51] Int. Cl.² ............................................. G01N 21/22
[52] U.S. Cl. ....................................................... 356/201
[58] Field of Search .......................... 356/201, 202, 246

[56] References Cited

U.S. PATENT DOCUMENTS 3,627,431  12/1971  Komarniski .......................... 356/246
3,773,426  11/1973  Mudd .................................. 356/246

Primary Examiner—John K. Corbin
Assistant Examiner—R. A. Rosenberger
Attorney, Agent, or Firm—Donald J. Perrella

[57] ABSTRACT

Apparatus and method for automatically reading a microtiter plate comprises a light source, a photo sensor, means enabling the photo sensor to measure light transmittance and means for recording and processing the measurements.

9 Claims, 3 Drawing Figures

U.S. Patent  Sept. 19, 1978  4,115,010
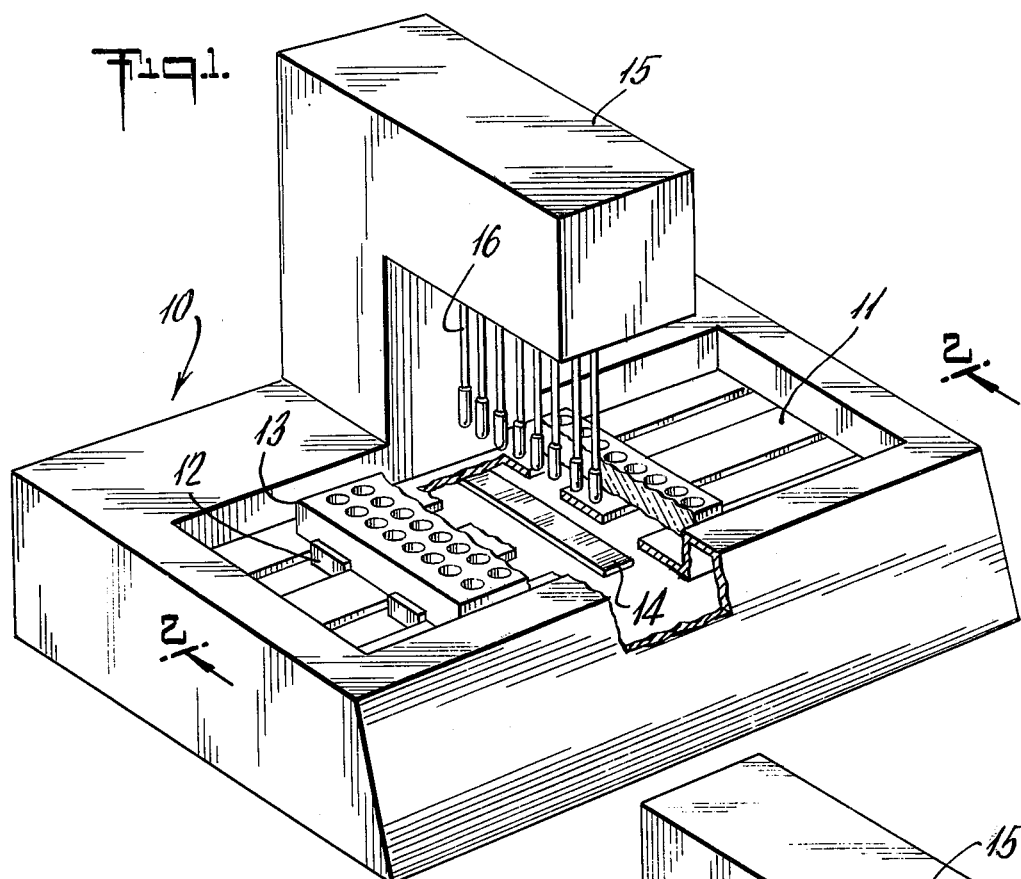
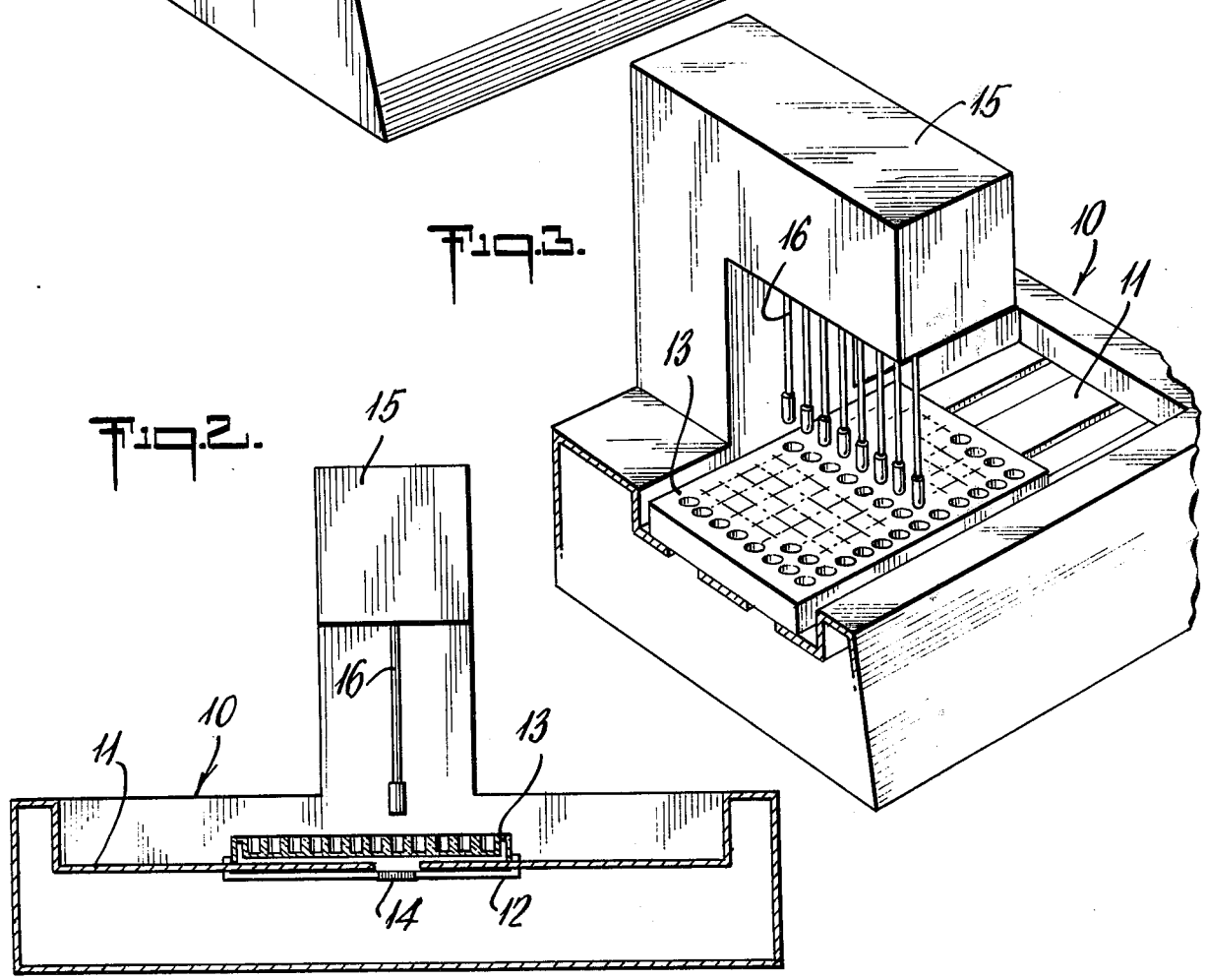

AUTOMATED PLATE READER

BACKGROUND OF THE INVENTION

Conventional dilution assays such as bacterial, serological, neutralization and CPE involve determining an effect or lack of an effect in a plurality of wells of a microtiter plate. Typically the plate has 96 wells each of which must be inspected separately by a highly skilled individual. This procedure is very time consuming, tedious and expensive.

OBJECTS OF THE INVENTION

It is an object of the present invention to provide an apparatus and method for determining the dilution end point. Another object is to provide an apparatus and method for automatically determining the dilution end point. Yet another object is to provide a method for automatically determining the dilution end point and automatically recording and processing the data. These and other objects of the present invention will be apparent from the following description.

SUMMARY OF THE INVENTION

The present invention is directed to apparatus and method for automatically determining the dilution end point in wells such as in a microtiter plate by measuring the light transmittance through the wells, which is a function of the presence, absence or degree of the effect being observed, and automatically recording and processing the light transmittance measurements.

BRIEF DESCRIPTION OF THE DRAWINGS

FIG. 1 is a perspective view of apparatus of the present invention;

FIG. 2 is a section along the line 2—2 of FIG. 1; and

FIG. 3 is a side elevation.

DETAILED DESCRIPTION

The method of the present invention is applicable to all dilution assays, one example of which is the CPE assay.

In the standard cytopatholigic effect (CPE) assay, the microtiter assay plate consists of 96 wells comprising 12 separate 8-well dilution assays. Each well contains the same concentration of cells while the concentration of virus diminishes in predetermined ratio in each succeeding well of a particular 8-well assay. In operation the cells and virus are planted in the wells of the microtiter plate and incubated for a time sufficient to permit a cell sheet to form and for the virus to act. The wells are then drained and stain is added to enhance the opacity of the remaining cells. The wells are then dried, the separate 8-well dilution assays are read and the resultant numbers statistically treated to get the composite viral titer.

The light source is an electroluminescent strip long enough to illuminate simultaneously the first well of each of the 12 assays being run on the particular microtiter plate, and wide enough to illuminate the first well in each assay row. Preferably the photoluminescent source has peak output corresponding to the peak absorption of the dye used to stain the cells in the CPE assay. The dye may be any protein stain suitable for staining a cell sheet. Carbolfuchsin stain is a preferred dye. When this dye is used, the photoluminescent source chosen has a peak output of about 550 m$\mu$ as the dye has a peak absorption at about 550 m$\mu$. A specific source of such a photoluminescent sheet is Grimes Manufacturing, Urbana, Ohio.

The photo sensors also have certain characteristics which are important to the success of the system. The photo sensor preferably has a peak sensitivity corresponding to that of the photoluminescent source. The photo sensor preferably also has a recovery lag (light history effect) which makes it insensitive to background "noise" such as the 60 cycle oscillation of the photoluminescent light source. This eliminates high frequency noise from affecting the assay reading. The photo sensors are adapted in size and shape to fit into the well to be analyzed and to permit the sensing surface to contact the cell surface being measured. A specific suitable photosensor is CL 605L, manufactured by Clairex Corp., Mt. Vernon, New York, which has a peak sensitivity at about 550 m$\mu$.

The apparatus of the present invention comprises a chassis 10 having a recess 11 therein containing a microtiter plate holder 12. The holder is adapted to receive a microtiter plate 13 and to be advanced sequentially in predetermined distances so as to bring one row of wells at a time over the photoluminescent strip 14 shown beneath the partially broken away microtiter plate 13. The strip 14 is located below the microtiter plate and disposed within the chassis so as to shine upwards through the microtiter plate. The means to advance the microtiter plate holder a predetermined distance of one row at a predetermined interval of time is not illustrated or described as it is old in the art and does not form part of the present invention. Such a mechanism is found, for instance, in the apparatus for automatically diluting the wells of a microtiter plate manufactured by Cooke Engineering Company, Alexandria, Virginia.

Mounted above the chassis of the plate manipulator is a photo sensor supporting means 15 having a plurality of photo resistors 16, means for lowering the photo resistors into the wells of the microtiter plate and for raising the photo resistors therefrom. The raising and lowering means are synchronized in known manner with the movement of plate holder 12 whereby the plate holder is stopped directly beneath the photo sensors which are then lowered into the wells. The photo resistors are then raised and the microtiter plate advanced one row to begin another cycle. The means to raise and lower the photo resistors into the wells is not illustrated or described as it is old in the art and does not form part of the present invention. Such a mechanism is found, for instance, in the above-mentioned apparatus for performing serial dilutions in the wells of a microtiter plate and the replacement of the diluting means by a photo sensor is an obvious expedient. When lowered into the well the photo sensor contacts the cell sheet and measures the light transmitted through the well by photoluminescent strip 14. The photo resistor is connected to a digital computer (not shown) which records the light transmittance measurements. The computer is programed to perform a standard statistical technique, e.g., analysis of variants or curve fitting or any other statistical method adapted to determine presence or absence of CPE in each well.

A feature of the present invention is the fact that the light source and light responsive means are identical for each assay. That is to say, the same portion or area of the photoluminescent strip illuminates each of the wells of a particular assay, and the same photo sensor is employed to determine the CPE of each well of a particular assay. In this way any discrepancy in readings due to variability in the photoluminescent strip or the photo sensor are eliminated.

What is claimed is:

1. Apparatus adapted to carry out one or more viral assays simultaneously comprising
   carrier means including a plurality of test wells for holding and transporting a dry cell sheet which has been stained after undergoing viral attack, the concentration of virus in each well of an individual assay being different from that of every other well so as to provide a serial titration of virus concentration,
   a light source disposed beneath the virus growth carrier means,
   a plurality of photo sensors disposed above the virus growth carrier means, each sensor being energized when the light from the light source passes through the test well below that sensor,
   means for lowering the photo sensors into the test wells and measuring light transmittance of the dry, stained cell sheet when the photo sensors are in lowered position, and for raising the photo sensors therefrom,
   and digital computer means for recording the light transmittance measurements of the photo sensors.

2. Apparatus according to claim 1 wherein the peak output of the light source corresponds to the peak sensitivity of the photo sensors.

3. Apparatus according to claim 1 wherein the light source is a photoluminescent strip having a peak output at about 550 mμ.

4. Apparatus according to claim 1 wherein the photo sensors have a peak sensitivity at about 550 mμ.

5. Apparatus according to claim 1 wherein each of the photo sensors reads only one assay sequence in the microtiter plate.

6. Apparatus according to claim 1 wherein the same portion of the light source is used for each assay.

7. Apparatus according to claim 1 wherein the photo sensors have a light recovery time adapted to render the photo sensors insensitive to detrimental noise signals.

8. A method for carrying out a viral assay comprising
   disposing between a light source and a photo sensor a plurality of dry cell sheets which have been stained after undergoing viral attack,
   moving the photo sensor into contact with the cell sheet,
   energizing the photo sensor by means of a light source adapted to pass light through the cell sheet toward the photo sensor,
   and recording the light transmittance measurement of the photo sensor when light passes through the cell sheet in a digital computer programmed to determine presence or absence of cytopathic effect.

9. A method according to claim 8 wherein two or more viral assays are carried out.

* * * * *